(12) United States Patent
Furo et al.

(10) Patent No.: US 10,028,915 B2
(45) Date of Patent: Jul. 24, 2018

(54) POLYVINYL ALCOHOL PARTICLES, PHARMACEUTICAL BINDER USING SAME, PHARMACEUTICAL TABLET, SUSTAINED-RELEASE PHARMACEUTICAL TABLET, AND METHOD FOR PRODUCING POLYVINYL ALCOHOL PARTICLES

(71) Applicant: THE NIPPON SYNTHETIC CHEMICAL INDUSTRY CO., LTD., Osaka (JP)

(72) Inventors: Chizuko Furo, Osaka (JP); Taiji Kanda, Osaka (JP); Koji Hara, Osaka (JP); Pradeep Ratilal Vavia, Mumbai (IN); Jasmin Dhirajlal Monpara, Mumbai (IN); Pankaj Hanumantrao Jadhav, Mumbai (IN)

(73) Assignee: THE NIPPON SYNTHETIC CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 15/328,580

(22) PCT Filed: Jul. 24, 2015

(86) PCT No.: PCT/JP2015/071168
§ 371 (c)(1),
(2) Date: Jan. 24, 2017

(87) PCT Pub. No.: WO2016/013675
PCT Pub. Date: Jan. 28, 2016

(65) Prior Publication Data
US 2017/0209377 A1    Jul. 27, 2017

(30) Foreign Application Priority Data
Jul. 25, 2014  (JP) ................................ 2014-152290

(51) Int. Cl.
| *A61K 9/20* | (2006.01) |
| *A61K 9/16* | (2006.01) |
| *A61K 31/155* | (2006.01) |
| *C08J 3/12* | (2006.01) |

(52) U.S. Cl.
CPC .......... *A61K 9/2027* (2013.01); *A61K 9/1635* (2013.01); *A61K 9/1682* (2013.01); *A61K 31/155* (2013.01); *C08J 3/12* (2013.01); *C08J 2329/04* (2013.01)

(58) Field of Classification Search
None
See application file for complete search history.

(56) References Cited

U.S. PATENT DOCUMENTS

| 4,990,335 A | 2/1991 | Bateman et al. |
| 5,070,126 A | 12/1991 | Toyonishi et al. |
| 2001/0024322 A1 | 9/2001 | Harita et al. |

FOREIGN PATENT DOCUMENTS

| EP | 2335697 A1 | 6/2011 |
| EP | 2674149 A1 | 12/2013 |
| JP | S42-000947 B | 1/1967 |
| JP | S51-93992 A | 8/1976 |
| JP | H02-502720 A | 8/1990 |
| JP | H02-225506 A | 9/1990 |
| JP | H03-033130 A | 2/1991 |
| JP | H11-236417 A | 8/1999 |
| JP | 2001-311828 A | 11/2001 |
| JP | 2005-298347 A | 10/2005 |
| JP | 2008-222839 A | 9/2008 |
| JP | 2013-028712 A | 2/2013 |
| JP | 2013-087074 A | 5/2013 |
| JP | 2013-241341 A | 12/2013 |

OTHER PUBLICATIONS

Kanda et al., "H Spin Diffusion of Polyvinyl Alcohol Film-n-Decane System", Proc. Soc. Solid State NMR Mater, 2010, No. 47, pp. 43.
International Search Report issued with respect to Application No. PCT/JP2015/071168, dated Oct. 27, 2015.
International Preliminary Report on Patentability issued with respect to Application No. PCT/JP2015/071168, dated Jan. 31, 2017.
Extended European Search Report from Application No. 15825381.5 dated Jan. 25, 2018.

*Primary Examiner* — Bong-Sook Baek
(74) *Attorney, Agent, or Firm* — Greenblum & Bernstein, P.L.C.

(57) ABSTRACT

Provided herein is a polyvinyl alcohol fine particle suitable for a pharmaceutical binder for obtaining a pharmaceutical tablet of properties including good sustained release, high hardness, and excellent friability. The polyvinyl alcohol fine particle of the present invention contains 25 mol % or more of a gauche structure in polyvinyl alcohol molecules within a 0.8-nm region inside the particle from the particle surface.

10 Claims, 3 Drawing Sheets

[Fig. 1]

VACP : Variable Amplitude Closs Polarization
DD : Dipole Decoupling
PD : Post Delay
FID : Free Induction Decay

POLYVINYL ALCOHOL PARTICLES, PHARMACEUTICAL BINDER USING SAME, PHARMACEUTICAL TABLET, SUSTAINED-RELEASE PHARMACEUTICAL TABLET, AND METHOD FOR PRODUCING POLYVINYL ALCOHOL PARTICLES

TECHNICAL FIELD

The present invention relates to polyvinyl alcohol fine particles, pharmaceutical binders using same, pharmaceutical tablets, sustained-release pharmaceutical tablets, and a method for producing polyvinyl alcohol fine particles. Particularly, the invention relates to polyvinyl alcohol (hereinafter, also referred to simply as "PVA") fine particles that, when used as a pharmaceutical hinder, can produce pharmaceutical tablets of properties including good sustained release, high hardness, and excellent friability with a smooth surface. The invention also relates to pharmaceutical binders and pharmaceutical tablets consisting of the polyvinyl alcohol fine particles.

BACKGROUND ART

PVA is a water-soluble resin, and has been used in a wide range of applications by taking advantage of its characteristics. PVA is a powder or a granular solid in its product form, and widely used in various processes and applications typically after being dissolved in water.

Because of the conception that PVA is used after being dissolved in water, there are not many studies of PVA with regard to its characteristics in a product solid form.

However, a method that measures the surface condition of a film-like PVA is proposed recently. An analysis of a PVA film immersed in a non-solvent low-molecular liquid has revealed formation of larger numbers of intermolecular hydrogen bonds near the surface of PVA (see Non-Patent Document 1).

Use as an additive for pharmaceutical tablets is an example of PVA being directly used in solid form without being dissolved in water. Pharmaceutical tablet, a form of pharmaceutical preparations, is typically produced by tablet-forming. With respect to the method of tablet-forming, a granule obtained by granulating a powder mixture obtained by mixing various additive components with an effective ingredient (active ingredient) as a medicament, or the powder mixture is charged directly into a mortar, and molded into the desired size and shape by being compressed with pestle. The molded tablets are optionally coated with, for example, a cellulose compound or sugar, as required.

Examples of the additive components contained with the active ingredient in pharmaceutical tablets include: excipients (a component with no physiological activity, added to appropriately bulk up the formulation), binders (a component added to bind powder particles of raw materials, and to control the mechanical strength of the tablet), disintegrants (a component added to facilitate release of the active ingredient by disintegrating the tablet through expansion by absorbing moisture in the body), and lubricants (a component added to improve the fluidity of the powder for easy compression molding).

Among these additive components, the binder particularly has large impact on tablet strength. When the binder is not appropriately selected, there are problems such as molding failure, and tablet breaking occur after molding. The binder also affects the dissolution rate of active ingredient. Since the active ingredient is not easily absorbed if the tablet does not disintegrate when entering body, both the storage strength and the dissolution control upon administration are important and compatibility thereof is required. Particularly, sustained-release preparations, which are controlled to dissolve over a long time, have been actively developed since sustained-release preparations can improve the compliance by taking the medication less frequently, and, or prevent side effects by making the fluctuations of blood concentration smaller.

For example, Paten Document 1 discloses a binder using a polyvinyl alcohol copolymer of a specific average particle size. The binder is described as being most suitable for orally disintegrating tablets (OD tablets), and most suitable for direct tableting.

Patent Document 2 discloses that a polyvinyl alcohol copolymer is used for sustained-release preparations, and controlling dissolution over a long time is achieved by using it.

RELATED ART

Patent Document

Patent Document 1: JP-A-2013-087074
Patent Document 2: JP-A-2013-241341

Non-Patent Document

Non-Patent Document 1: T. Kanda and F. Horii., Proc. Soc. Solid State NMR Mater., No. 47, 43 (2010)

DISCLOSURE OF INVENTION

Technical Problem

The binder described in Patent Document 1 is suited for tableting, and can provide desirable immediate disintegrability for a tablet and release of active ingredient in a short time. While the binder is satisfactory in terms of above view points, it cannot control dissolution over a long time. The base material for matrix preparations described in Patent Document 2 is desirable in terms of sustained release of active ingredient, however, it is far from satisfactory in terms of the hardness and the friability of the obtained tablet. There accordingly is a need for a binder that has effect for both moldability and sustained release of a tablet.

Under these circumstances, the present invention is intended to provide PVA fine particles that, when used as a pharmaceutical binder in particular, can produce a pharmaceutical tablet of properties including good sustained release, high hardness, and excellent friability with a smooth surface. The invention is also intended to provide pharmaceutical binders, and pharmaceutical tablets.

Means for Solving the Problems

The present inventors conducted intensive studies to find a solution to the foregoing problems, and found that the problems can be solved with the use of polyvinyl alcohol fine particles having larger numbers of surface gauche structures than traditional polyvinyl alcohol fine particles. The present invention was completed on the basis of this finding.

Specifically, the present invention has the following configurations (1) to (11).

(1) A polyvinyl alcohol fine particle, comprising: 25 mol % or more of a gauche structure in polyvinyl alcohol molecules within a 0.8-nm region inside the particle from the particle surface.
(2) The polyvinyl alcohol fine particle according to (1), wherein the ratio (S1/S2) of an average degree of saponification (S1) of the polyvinyl alcohol fine particle to an average degree of surface saponification (S2) in the 0.8-nm region inside the particle from the particle surface is 1.10 or more.
(3) The polyvinyl alcohol fine particle according to (1) or (2), which is obtainable by pulverizing a dry powder of an unmodified polyvinyl alcohol consisting of solely a vinyl alcohol structure unit and a vinyl ester structure unit.
(4) The polyvinyl alcohol fine particle according to (3), wherein a 50% particle size of the dry powder of the unmodified polyvinyl alcohol is 50 to 2,000 μm.
(5) The polyvinyl alcohol fine particle according to any one of (1) to (4), wherein a 50% particle size of the polyvinyl alcohol fine particle is 1 to 200 μm.
(6) The polyvinyl alcohol fine particle according to any one of (1) to (5), which has an average degree of polymerization of 200 to 4,000.
(7) The polyvinyl alcohol fine particle according to any one of (1) to (6), comprising: an alkali metal salt in an amount of 0.001 to 2 mass % of the polyvinyl alcohol fine particle.
(8) A pharmaceutical binder, comprising: the polyvinyl alcohol fine particle of any one of (1) to 7).
(9) A pharmaceutical tablet, comprising: an active ingredient; and the pharmaceutical binder of (8).
(10) A sustained-release pharmaceutical tablet, comprising: an active ingredient; and the pharmaceutical hinder of (8).
(11) A method for producing a polyvinyl alcohol fine particle, comprising: washing and drying an unmodified polyvinyl alcohol obtained from a vinyl alcohol structure unit; and a vinyl ester structure unit, and pulverizing an obtained dry powder of the unmodified polyvinyl alcohol.

Advantageous Effects of Invention

The pharmaceutical binder of PVA fine particles of the present invention has large numbers of surface gauche structures, and this is believed to reduce surface crystallinity, and increase adhesion. A pharmaceutical tablet using the pharmaceutical binder of the present invention thus has properties including good sustained release, high hardness, and excellent friability, and the tableting surface condition is smooth.

The detailed mechanism by which large numbers of surface gauche structures provide the effects of the present invention remains unclear. However, considering that the gauche structure is a disrupted crystalline structure, the improved adhesion appears to be due to the disrupted crystalline structure on the surface of PVA fine particles. It is believed that the properties of the pharmaceutical tablet, including good sustained release, high hardness, and excellent friability with a smooth surface condition when tableting, are the result of the improved adhesion,

EMBODIMENTS FOR CARRYING OUT THE INVENTION

The present invention is described below in detail. As used herein, percent and part used with mass have the same meaning as percent or part by weight.

PVA Fine Particles

The PVA fine particles of the present invention includes a polyvinyl alcohol (hereinafter, also referred to simply as "PVA") having a vinyl alcohol structure unit, and a vinyl ester structure unit representing an unsaponified moiety. The PVA fine particles contain 25 mol % or more of a gauche structure in PVA molecules within a 0.8-nm region inside the PVA fine particles from the particle surface.

Preferably, with respect to f the PVA fine particles, the ratio (S1/S2) of the average degree of saponification (S1) to the average degree of surface saponification (S2) in a 0.8-nm region inside the particles from the particle surface is 1.10 or more.

A gauche structure refers to a torsional structure of a carbon-carbon bond in the main chain of PVA. A structure without torsion is planar, and is called a trans structure. Typically, a carbon-carbon bond in the main chain of PVA has either a gauche structure or a trans structure, and most of the carbon-carbon bonds have a trans structure.

A gauche structure results when a trans structure is rotated 60°. Because of the torsion, the crystallinity and the amount of hydrogen bond in the PVA molecules tend to decrease as the number of gauche structures increases.

The PVA fine particles of the present invention contain 25 mol % or more, preferably 27 mol % or more, particularly preferably 30 to 50 mol % of a gauche structure in PVA molecules in a 0.8-nm region inside the PVA fine particles from the particle surface.

There is a tendency that the effects of the present invention is hard to be obtained when this rate is too small.

The PVA fine particles containing 25 mol % or more of a gauche structure in PVA molecules within a 0.8-nm region inside the particles from the particle surface can be obtained by, for example, heating the PVA fine particle surface, pulverizing the PVA particles via collision, or washing the PVA fine particles with a solvent that does not dissolve PVA. These methods may be used in combination.

Among these, it is preferable that the PVA fine particles are washed with a solvent that does not dissolve PVA, dried, and pulverized via collision.

In the PVA fine particles of the present invention, the ratio (S1/S2) of the average degree of saponification (S1) of the whole particles to the average degree of surface saponification (52) in a 0.8-nm region inside the particles from the particle surface is preferably 1.10 or more, more preferably 1.10 to 1.50. There is a tendency that the effects of the present invention is hard to be obtained when this ratio is too small.

The PVA fine particles satisfying the ratio can be obtained by, for example, heating the PVA fine particle surface, pulverizing the PVA particles via collision, or washing the PVA fine particles with a solvent that does not dissolve PVA. These methods may be used in combination.

Among these, it is preferable that the PVA fine particles are washed with a solvent that does not dissolve PVA, dried, and pulverized via collision.

The following specifically describes the methods for measuring the gauche structure, and the average degree of surface saponification (S2). The methods for measuring are based on the techniques described in JP-A-2008-203159, and in T. Randa and F. Horii., Proc. Soc. Solid State NMR Mater., No. 47, 43 (2010).

Figure 1:
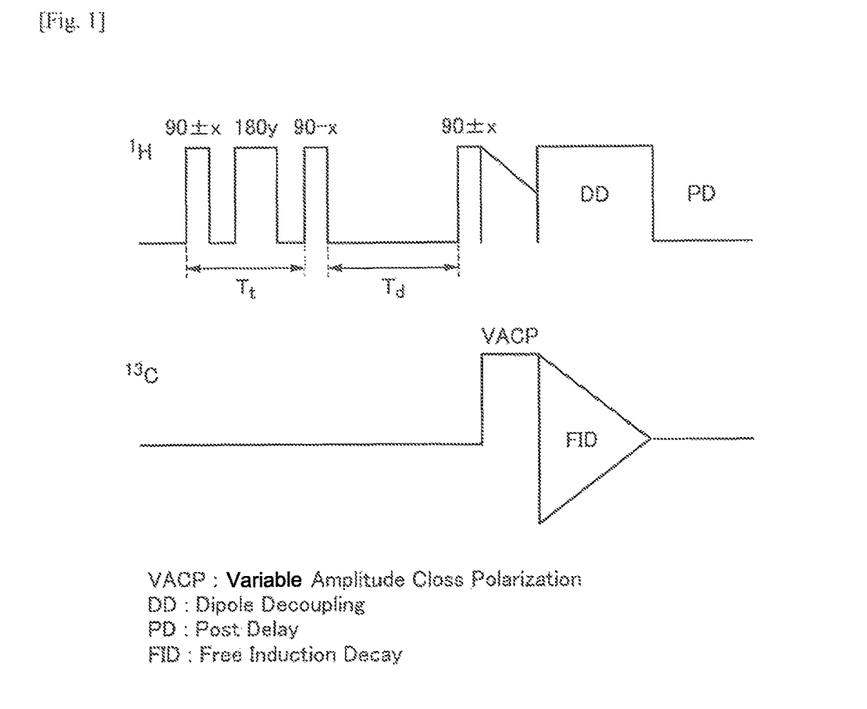
FIG. 1 is a diagram representing a pulse sequence used for NMR measurements performed in the present invention.

High-resolution solid-state NMR is used for structure analysis. The pulse sequence shown in FIG. 1 is used for measurement. Each of the parameters by used this is presented in Table 1 below. n-Decane is added in the same amount as the mass of the polyvinyl alcohol fine particles charged into a zirconia rotor having a diameter $\phi$ of 4 mm which is a sample tube.

TABLE 1

Measurement conditions

| Device Probe | Braker AVANCEIII 400WB CP/MAS probe ($\phi$ = 4 mm) |
|---|---|
| Temperature | Room temperature (22° C.) |
| Medium | n-decane |
| Observed nucleus | $^{13}C$ |
| Rotation of sample tube | 5,000 Hz |
| $^1H$ 90° pulse | 4.2 µs |
| Contact time | 350 µs |
| τt | 72 µs |
| τd | 1 ms, 20 ms, 50 ms, 100 ms |
| FID signal capture time | 14 ms |
| Runs | >3,000 |
| Observation center | 120 ppm |
| Observation range | 365 ppm |
| Waiting time | 20 s |

In Table 1, τt represents a portion due to the $^1H$ nucleus spin-spin relaxation of n-decane which is the polyvinyl alcohol fine particles and the medium. The magnetization of the polyvinyl alcohol fine particles cancels out with a τt of 60 µs or longer, whereas the magnetization of the n-decane remains to provide a condition for spin diffusion.

Increasing the τd time enhances the resonance line of a spectrum, and it is observed that spin diffusion occurs.

With the spin diffusion, the magnetization from the n-decane permeates into the polyvinyl alcohol fine particles through the particle surface. The spin diffusion time can be represented by a distance function of the formula (1) below. A spectrum obtained from a very short spin diffusion time represents a structure with a short distance L (nm) from the PVA fine particle surface into the particle, specifically a structure in the vicinity of the surface.

$$L=(a \times D \times \tau d)^{0.5} \quad (1)$$

(In formula (1), a is a constant with the value 4/3, the diffusion constant D has an assumed value of 0.5 nm/ms, and τd represents the spin diffusion time (ms).)

It is to be noted that the constants a and D are described in K. Masuda, M. Adachi, H. Yamamoto, H. Koji, and F. Horii, Solid State NMR, 23, 198 (2003), and in J. R. Havens and D. L. VanderHart, Macromolecules, 23, 1663 (1985).

Solving the equation (1) for L by substituting the constants with the foregoing numbers and the τd with the minimum value, 1, of spin diffusion time (ms) yields a value of 0.8 nm as the distance from the PVA fine particle surface into the particle when an effective value of is the first decimal place. The number is the least measurable value, and represents a distance corresponding to a single molecule of PVA.

The peaks in the obtained spectrum are separated at 46 ppm ($CH_2$ with a trans-trans structure in the main chain of polyvinyl alcohol), 41 ppm ($CH_2$ with a trans-gauche structure in the main chain of polyvinyl alcohol), 36 ppm ($CH_2$ with a gauche-gauche structure in the main chain of polyvinyl alcohol), and 21 ppm ($CH_3$ in the residual acetyl of polyvinyl alcohol), using a Gaussian function. The area of each peak is then calculated.

The content of the gauche structure in the PVA molecules residing in a 0.8-nm region inside the particles from the particle surface is calculated according to the following formula (2).

$$\text{Gauche structure (mol \%)}=100\times(B/2+C)/(A+B+C) \quad (2)$$

(In formula (2), A represents the peak area at 46 ppm, B represents the peak area at 41 ppm, and C represents the peak area at 36 ppm.)

The degree of surface saponification is calculated according the following formula (3).

$$\text{Degree of saponification (mol \%)}=100\times(1-D/(A+B+C)) \quad (3)$$

(In formula (3), A represents the peak area at 46 ppm, B represents the peak area at 41 ppm, C represents the peak area at 36 ppm, and D the peak area at 21 ppm.)

The following re specifically describes the method of production of PVA fine particles.

The PVA which is a feedstock of PVA fine particles may be obtained through saponification of, for example, a polyvinyl ester polymer polymerized from vinyl ester monomers.

Examples of the vinyl ester monomers include vinyl formate, vinyl acetate, vinyl propionate, vinyl valerate, vinyl butyrate, vinyl isobutyrate, vinyl pivalate, vinyl caprate, vinyl laurate, vinyl stearate, vinyl benzoate, and vinyl versatate. Preferred for practicality is vinyl acetate.

It is also possible to use saponification products of copolymers of the vinyl ester monomers and monomers that are copolymerizable with the vinyl ester monomers, provided that such copolymers do not inhibit the effects of the present invention. Examples of such copolymerizable monomers include:

olefins such as ethylene, propylene, isobutylene, α-octene, α-dodecene, and α-octadecene;

hydroxyl-containing α-olefins such as 3-buten-1-ol, 4-penten-1-ol, 5-hexen-3,4-dihydroxy-1-butene, and derivatives thereof such as acylates;

unsaturated acids such as acrylic acid, methacrylic acid, crotonic acid, maleic acid, a maleic acid anhydride, itaconic acid, and undecylenic acid, and salts, monoesters, and dialkyl esters thereof;

nitriles such as acrylonitrile, and methacrylonitrile;

amides such as diacetoneacrylamide, acrylamide, and methacrylamide;

olefin sulfonic acids such as ethylene sulfonic acid, allyl sulfonic acid, methallyl sulfonic acid, and salts thereof;

vinyl compounds such as alkyl vinyl ethers, dimethylallyl vinyl ketone, N-vinyl pyrrolidone, vinyl chloride, vinyl ethylene carbonate, 2,2-dialkyl-4-vinyl-1,3-dioxolan, and glycerine monoallyl ether;

substituted vinyl acetates such as isopropenyl acetate, and 1-methoxy vinyl acetate;

vinylidene chloride, 1,4-diacetoxy-2-butene, 1,4-dihydroxy-2-butene, and vinylene carbonate.

The content of the copolymerizable monomer is typically 10 mol % or less, preferably 5 mol % or less, particularly preferably 1 mol % or less with respect to the total polymer amount. In the present invention, the PVA is preferably an unmodified PVA of solely a vinyl alcohol structure unit, and a vinyl ester structure unit representing an unsaponified moiety.

The method of polymerization of the vinyl ester monomer and the copolymerizable monomer is not particularly limited, and known methods such as bulk polymerization, solution polymerization, suspension polymerization, dispersion polymerization, and emulsion polymerization may be used. Typically, solution polymerization is used.

Typical examples of the solvent used for the polymerization include aliphatic alcohols of 1 to 4 carbon atoms such as methanol, ethanol, isopropyl alcohol, n-propanol, and butanol, and ketones such as acetone, and methyl ethyl ketone. Preferred for industrial applications is methanol.

The polymerization reaction is performed with known radical polymerization catalysts such as azobisisobutyronitrile, acetyl peroxide, benzoyl peroxide, and lauroyl peroxide, or various known cold activation catalysts. The reaction temperature is selected from a range of from about 35° C. to the boiling point.

The polyvinyl ester polymer is saponified either continuously or in a batch. The saponification may be alkali saponification or acid saponification. In industrial applications, the polymer is dissolved in alcohol, and saponified in the presence of an alkali catalyst. Examples of the alcohol include methanol, ethanol, and butanol. The polymer concentration in alcohol is selected from a range of from 20 to 60 mass %. About 0.3 to 10 mass % of water may be added, as required. It is also possible to add various solvents, for example, such as esters (e.g., methyl acetate), benzene, hexane, and DMSO (dimethylsulfoxide).

Specific examples of the saponification catalyst include alkali catalysts, for example, such as hydroxides of alkyl metals (e.g., sodium hydroxide, potassium hydroxide, sodium methylate, sodium ethylate, and potassium methylate), and alcoholate. Preferably, the catalyst is used in a 1 to 100 millimolar equivalent with respect to the monomer.

After saponification, the obtained polyvinyl ester polymer is washed with a washing liquid. Examples of the washing liquid include alcohols such as methanol, ethanol, isopropyl alcohol, and butanol. Preferred for washing efficiency and drying efficiency is methanol.

The washing may be performed continuously (e.g., rotational washing with a cylinder, counterflow contact washing, and centrifugal spray washing). However, batch washing is typically employed. The stirring method (stirring device) used for washing may be, for example, a screw blade, a ribbon blender, or a kneader. The bath ratio (mass of washing liquid/mass of polyvinyl ester polymer particles) is typically 1 to 30, particularly preferably 2 to 20. A large washing device will be required, and the cost tends to increases when the bath ratio is excessively large. An excessively small bath ratio often leads to poor washing performance, and frequent washing.

The washing temperature is typically 10 to 80° C., particularly preferably 20 to 70° C. An excessively high temperature tends to increase the vaporization of the washing liquid, and necessitate reflux equipment. The washing efficiency tends to decrease when the temperature is too low. The washing time is typically 5 minutes to 12 hours, particularly preferably 30 minutes to 4 hours. An excessively long washing time tends to cause poor production efficiency, whereas insufficient washing tends to result when the washing time is too short. The washing is performed typically 1 to 10 times, particularly preferably 1 to 5 times. Productivity suffers, and the cost tends to increase when washing is performed too frequently.

The washed polyvinyl ester polymer particles are dried with, for example, hot air, either continuously or in a hatch, to obtain a PVA powder. The drying temperature is typically 50 to 150° C., preferably 60 to 130° C., further preferably 70 to 110° C. An excessively high drying temperature tends to cause heat deterioration of the polyvinyl ester polymer particles, whereas the drying often takes a long time when the drying temperature is too low. The drying time is typically 1 to 48 hours, particularly preferably 2 to 36 hours. An excessively long drying time tends to cause heat deterioration of the polyvinyl ester polymer particles, whereas an excessively short drying time tends to cause insufficient drying, or necessitate high-temperature drying.

The content of the solvent in the dried unmodified PVA powder is typically 0 to 10 mass %, preferably 0.1 to 5 mass %, and further preferably 0.1 to 1 mass %.

The unmodified PVA powder contains an alkali metal salt of acetic acid originating in the alkali catalyst used for saponification. The content of the alkali metal salt is typically 0.001 to 2 mass %, preferably 0.005 to 1 mass %, further preferably 0.01 to 0.1 mass % with respect to the unmodified PVA powder.

The content of the alkali metal salt may be adjusted by, for example, adjusting the amount of the alkali catalyst used for saponification, or by washing the PVA with alcohols such as ethanol and methanol.

In the present invention, the alkali metal salt may be quantified by, for example, dissolving the PVA powder in water, and determining the content through neutralization titration with hydrochloric acid, using methyl orange as an indicator.

The PVA used in the present invention has an average degree of polymerization of preferably 200 to 4,000, more preferably 400 to 3,500, further preferably 500 to 3,000. When the average degree of polymerization is too small, it may not be possible to obtain sufficient adhesion or sustained release in the tablet. On the other hand, moldability may suffer when the average degree of polymerization is too large, as it makes it difficult to mix the PVA with other components such as an active ingredient, and an excipient. In the present invention, the average degree of polymerization is a measured value according to the JIS K6726 method.

The viscosity of a 4 mass % aqueous solution of PVA at 20° C. is preferably 1.5 to 100 mPa·s, more preferably 4 to 80 mPa·s, further preferably 5 to 70 mPa·s. When the viscosity of the 4 mass % aqueous solution is too large, moldability may suffer as the solvent causes gelation, makes mixing difficult during production. On the other hand, sufficient adhesion or sustained release may not be obtained when the viscosity of the 4 mass % aqueous solution is too small. In the present invention, the viscosity of the 4 mass % aqueous solution at 20° C. is a measured value according to the JIS K6726 method.

The PVA used in the present invention has a degree of saponification of preferably 70 to 100 mol %, more preferably 80 to 95 mol %, further preferably 85 to 90%. When the degree of saponification is too low, it may not be possible to maintain sustained release. When the degree of saponification is too high, quick disintegration may occur due to the lack of adhesion. In the present invention, the degree of saponification is a measured value according to the JIS K6726 method.

Typically, the predominant form of bonding in the main chain of PVA is the 1,3-diol linkage, and the 1,2-diol linkage accounts for only about 1.5 to 1.7 mol %. However, the PVA used in the present invention may be one in which the 1,2-diol linkage has been increased to 1.7 to 3.5 mol % by increasing the polymerization temperature of the polymerization of the vinyl ester monomer.

In the present invention, the unmodified PVA powder after drying and before pulverization has a 50% particle size of preferably 50 to 2,000 μm, more preferably 60 to 1,500 μm, further preferably 70 to 1,000 μm. Handling in the washing or pulverization of PVA may suffer when the 50% particle size of the unmodified PVA powder is too small. On the other hand, washing efficiency and pulverization efficiency may suffer when the 50% particle size of the unmodified PVA powder is too large. The 50% particle size is the diameter at 50% in the cumulative value (cumulative distribution) obtained from the measured laser diffraction volume distribution by particle size.

It is particularly preferable in the present invention to pulverize the PVA dry powder into PVA fine particles as the pharmaceutical binder of the present invention.

Conceivably, the surface of the PVA dry powder undergoes changes due to external factors such as washing and drying in the production of the unmodified PVA dry powder.

The unmodified PVA dry powder is pulverized to expose the inside and to be the PVA fine particles that have undergone surface changes. A tablet produced by adding the PVA fine particles as a pharmaceutical binder can have improvement in hardness, moldability, and sustained release.

In the pulverization step, the PVA powder is pulverized into the desired particle size to obtain the PVA fine particles of the present invention. From the standpoint of the moldability, surface smoothness, and sustained release of the tablet, the 50% particle size of the PVA fine particles is preferably 1 to 200 μm, more preferably 10 to 180 μm, further preferably 15 to 150 μm. When the 50% particle size of the pulverized PVA fine particles is too small, the powder mixture cannot have desirable fluidity, and it often becomes difficult to produce a uniform preparation. When the 50% particle size of the pulverized PVA fine particles is too large, the surface area becomes smaller, and the adhesion and sustained release tend to suffer.

The PVA fine particles have the same average degree of polymerization as the PVA before pulverization. Specifically, the PVA fine particles has an average degree of polymerization of preferably 200 to 4,000, more preferably 400 to 3,500, further preferably 500 to 3,000. When the average degree of polymerization is too small, the tablet may fail to have sufficient adhesion and sustained release. On the other hand, moldability may suffer when the average degree of polymerization is too large, as it makes it difficult to mix the PVA fine particles with other components such as an active ingredient, and an excipient.

The method for pulverizing the PVA dry powder is not particularly limited, and the PVA dry powder may be pulverized by using, for example, a roller mill, a bead mill, a ball mill, a jet mill, a hammer mill, or a pin mill, or by grinding pulverization or collision pulverization. A method using collision pulverization is preferred because it involves only limited heat on the obtained PVA fine particles. Parameters such as pulverization temperature and pulverization time may be appropriately set according to the means of pulverization, as long as the desired particle size is obtained.

For example, collision pulverization is a method that pulverizes the PVA dry powder via self collision in a high-speed swirling airflow. This method is preferred in the present invention because it involves only small air friction and small temperature increase, and reduces heat deterioration of the PVA fine particles with the reduced abrasion.

In the pulverization method using collision pulverization, the pulverization temperature is preferably 10 to 100° C., more preferably 20 to 80° C.

The PVA fine particles of the present invention obtained in the manner described above can preferably be used as a pharmaceutical binder used as an additive of pharmaceutical tablets.

Active Ingredient

Examples of the active ingredients used in the present invention include antipyretic analgesic antiphlogistics, nutrient and tonic supplements, psychotropics, antidepressants, antianxiety drugs, hypnosedatives, anticonvulsants, CNS-acting drugs, brain metabolism improving agents, brain circulation improving agents, antiepileptic agents, sympathomimetic drugs, gastrointestinal drugs, acid suppressants, anti-ulcerogenic drugs, cough medicines, antiemetics, anapnoics, bronchodilators, allergic drugs, antihistamine agents, agents for dental and oral use, cardiants, agents for cardiac arrhythmia, diuretics, hypertension drugs, vasoconstrictors, coronary vasodilators, peripheral vasodilators, blood coagulation inhibitors, hyperlipidemias agents, cholagogues, antibiotics, chemotherapeutic agents, diabetes drugs, osteoporosis drugs, antirheumatics, skeletal muscle relaxants, antispasmodics, hormonal agents, alkaloid drugs, sulfa drugs, arthrifuges, and antineoplastics.

Examples of the antipyretic analgesic antiphlogistics include acetaminophen, aspirin, ibuprofen, ethenzamide, diphenhydramine hydrochloride, dl-chlorpheniramine maleate, diclofenac sodium, dihydrocodeine phosphate, salicylamide, aminopyrine, noscapine, methylephedrine hydrochloride, phenylpropanolamine hydrochloride, serrapeptase, lysozyme chloride, tolfenamic acid, mefenamic acid, flufenamic acid, ketoprofen, indometacin, bucolome, pentazocine, caffeine, and anhydrous caffeine.

Examples of the nutrient and tonic supplements include vitamins such as vitamin A, vitamin B1 (e.g., dibenzoylthiamine, and fursulthiamine hydrochloride), vitamin B2 (e.g., riboflavin butyrate), vitamin B6 (e.g., pyridoxine hydrochloride), vitamin B12 (e.g., hydroxocobalamin acetate, and cyanocobalamin), vitamin C (e.g., ascorbic acid, and sodium L-ascorbate), vitamin D, and vitamin E (e.g., d-α-tocopherol acetate); minerals such as calcium, magnesium, and iron; proteins, amino acids, oligosaccharides, and crude drugs.

Examples of the psychotropics include chlorpromazine, and reserpine.

Examples of the antidepressants include amphetamine, imipramine, and maprotiline hydrochloride.

Examples of the antianxiety drugs include diazepam, alprazolam, and chlordiazepoxide.

Examples of the hypnosedatives include estazolam, diazepam, nitrazepam, perlapine, and phenobarbital sodium.

Examples of the anticonvulsants include scopolamine hydrobromide, diphenhydramine hydrochloride, and papaverine hydrochloride.

Examples of the CNS-acting drugs include citicoline.

Examples of the brain metabolism improving agents include meclofenoxate hydrochloride.

Examples of the brain circulation improving agents include vinpocetine.

Examples of the antiepileptic agents include phenitoin, and carbamazepine.

Examples of the sympathomimetic drugs include isoproterenol hydrochloride.

Examples of the gastrointestinal drugs include stomach digestive aids such as diastase, saccharated pepsin, a scopolia extract, cellulase AP3, lipase AP, and cinnamon oil; and antiflatulents such as berberine chloride, resistant lactic acid bacteria, and bifidobacteria.

Examples of the acid suppressants include magnesium carbonate, sodium bicarbonate, magnesium aluminometasilicate, synthetic hydrotalcite, precipitated calcium carbonate, and magnesium oxide.

Examples of the anti-ulcerogenic drugs include lansoprazole, omeprazole, rabeprazole, cimetidine, famotidine, and ranitidine hydrochloride.

Examples of the cough medicines include cloperastine hydrochloride, dextromethorphan hydrobromide, theophylline, guaiacol potassium sulfonate, gualfenesin, and codeine phosphate.

Examples of the antiemetics include difenidol hydrochloride, and metoclopramide.

Examples of the anapnoics include levallorphan tartrate.

Examples of the bronchodilators include theophylline, and sulbutamol sulfate.

Examples of the allergic drugs include amlexanox, and seratrodast.

Examples of the antihistamine agents include diphenhydramine hydrochloride, promethazine, isothipendyl hydrochloride, and dl-chlorpheniramine maleate.

Examples of the agents for dental and oral use include oxytetracycline, triamcinolone acetonide, chlorhexidine hydrochloride, and lidocaine.

Examples of the cardiants include digoxin, and caffeine.

Examples of the agents for cardiac arrhythmia include procainamide hydrochloride, propranolol hydrochloride, and pindolol.

Examples of the diuretics include furosemide, isosorbide, and hydrochlorothiazide.

Examples of the hypertension drugs include captopril, delapril hydrochloride, hydralazine hydrochloride, labetalol hydrochloride, manidipine hydrochloride, candesartan cilexetil, methyldopa, and perindopril erbumine.

Examples of the vasoconstrictors include phenylephrine hydrochloride.

Examples of the coronary vasodilators include carbocromen hydrochloride, molsidomine, and verapamil hydrochloride.

Examples of the peripheral vasodilators include cinnarizine.

Examples of the blood coagulation inhibitors include dicumarol.

Examples of the hyperlipidmias agents include cerivastatin sodium, simvastatin, pravastatin sodium, and an atorvastatin calcium hydrate.

Examples of the cholagogues include dehydrocholic acid, and trepibutone.

Examples of the antibiotics include cephem antibiotics such as cephalexin, amoxicillin, cefaclor, pivmecillinam hydrochloride, cefotiam hexetil hydrochloride, cephadroxil, cefixime, cefditoren pivoxil, cefteram pivoxil, and cefpodoxime proxetil; monobactam antibiotics such as synthetic anti-microbial agent carumonam sodium, including ampicillin, ciclacillin, nalidixic acid, and enoxacin; and penem and carbapenem antibiotics.

Examples of the chemotherapeutic agents include sulfamethizole.

Examples of the diabetes drugs include glymidine sodium, glipizide, phenformin hydrochloride, buformin hydrochloride, metformin, metfomin hydrochloride, tolbutamide, voglibose, pioglitazone hydrochloride, glibenclamide, and troglitazone.

Examples of the osteoporosis drugs include ipriflavone.

Examples of the skeletal muscle relaxants include methocarbamol.

Examples of the antispasmodics include meclizine hydrochloride, and dimenhydrinate.

Examples of the antirheumatics include methotrexate, and bucillamine.

Examples of the hormonal agents include liothyronine sodium, dexamethasone sodium phosphate, prednisolone, oxendolone, and leuprorelin acetate.

Examples of the alkaloid drugs include opium, morphine hydrochloride, ipecacuanha, oxycodone hydrochloride, opium alkaloids hydrochlorides, and cocaine hydrochloride.

Examples of the sulfa drugs include sulfisomidin, and sulfamethizole.

Examples of the arthrifuges include allopurinol, and colchicine.

Examples of the antineoplastics include 5-fluorouracil, uracil, and mitomycin.

The content of the active component is appropriately adjusted according to bioavailability. The active component may be diluted with diluents commonly used in the field of medicine and food. The active component may be one that has been treated to mask bitterness.

Other Additives

Various additives may be added to the pharmaceutical tablet of the present invention, provided that it is not detrimental to the effects of the present invention. Examples of such additives include excipients, disintegrants, pH adjusters, fluidizers, surfactants, colorants, sweeteners, and coating agents.

The excipient may be one or two or more components selected from, for example, sugar alcohols, sugars, calcium phosphate, crystalline cellulose, starch, sodium phosphate, and gelatin. The preferred excipients are sugar alcohols, and sugars.

Examples of the sugar alcohols include mannitol, erythritol, xylitol, sorbitol, and maltitol. Examples of the sugars include glucose, fructose, lactose, sucrose, trehalose, maltose, and oligosaccharides.

Examples of the disintegrants include carmellose calcium, carboxymethyl starch sodium, croscarmellose sodium, crospovidone, celluloses and derivatives thereof, and starches and derivatives thereof.

Examples of the pH adjusters include citric acid and salts thereof, phosphoric acid and salts thereof, carbonic acid and salts thereof, tartaric acid and salts thereof, fumaric acid and salts thereof, acetic acid and salts thereof, amino acids and salts thereof, succinic acid and salts thereof, and lactic acid and salts thereof.

Examples of the fluidizers include, light anhydrous silicic acid, hydrous silicon dioxide, titanium oxide, stearic acid, a corn gel, and a heavy anhydrous silicic acid.

Examples of the surfactants include phospholipids, glycerin fatty acid esters, polyoxyethylene fatty acid esters, sorbitan fatty acid esters, polyethylene glycol fatty acid esters, polyoxyethylene hydrogenated castor oil, polyoxyethylene alkyl ethers, sucrose fatty acid esters, sodium lauryl sulfate, polysorbates, sodium hydrogen phosphates, and potassium hydrogen phosphates.

Examples of the colorants include iron sesquioxide, yellow iron sesquioxide, food yellow 5, food yellow 4, aluminum chelate, titanium oxide, and talc.

Examples of the sweeteners include saccharin, aspartame, acesulfame potassium, thaurnatin, and sucralose.

Examples of the coating agents include hydroxypropyl cellulose, hydroxypropyl methylcellulose, methylcellulose, polyvinyl alcohol, polyvinylpyrrolidone-ethyl acrylate, a methyl methacrylate copolymer dispersion, hydroxypropyl methylcellulose acetate succinate, and a methacrylic acid copolymer.

Pharmaceutical Tablet

The pharmaceutical tablet of the present invention is produced by mixing the foregoing components, followed by tablet compression, either directly or after being granulated.

The molding may be performed by using any of the methods commonly used for the compression molding of solid preparations in the field of medical drug products, including methods using a rotary tableting machine, and methods using a single-press tableting machine. For example, the pharmaceutical tablet of the present invention may be produced by using a direct powder compression method in which the components are compressed after being uniformly mixed, or a wet or dry granulation compression method in which the components are compressed as granules after being granulated by a wet or dry method.

Preferred for improved fluidity and mixture uniformity is the wet granulation compression method.

The wet granulation method is not particularly limited, as long as the components are granulated. The wet granulation method may be appropriately selected from known methods according to the intended use. Examples of such methods include wet disintegration, extrusion, a fluidized bed, and stirring. Among these, preferably, the wet granulation method is, for example, a stirring granulation method, or a fluidized bed granulation method, more preferably the stirring granulation method.

The device used for granulation is not particularly limited, and may be appropriately selected according to the intended use. Examples of the granulation device include a stirring granulation device (for example, Rapid Mixer Granulator available from Gem Pharma Machineries, and Vertical Granulator available from Powrex Corporation), and a fluidized bed granulation device (for example, a tumbling fluidized coating device MP-01 available from Powrex Corporation).

In the granulation step, the components are weighed, sieved and pulverized, and mixed in a granulator in a dry state. For granulation, it is preferable to add water or a solvent, or a mixture of water and a solvent to the powder mixture. The solvent may be appropriately selected according to the properties of the effective ingredient. Examples of the solvent include alcohols such as ethanol, butanol, and isopropyl alcohol. Preferred is isopropyl alcohol.

The granulated material is then subjected to tablet compression. The tablet compression may be performed by using various tableting machines, for example, such as the model HT-APSS, HT-AP-MS, HT-X-SS, and HT-X-MS available from Hata Tekkosho Co., Ltd., and VIRGO, AQUARIUS, and LIBRA available from Kikusui Seisakusho.

The pharmaceutical tablet may have any shape, including an ellipsoid, a column, a doughnut, and a sphere.

EXAMPLES

The following describes the present invention in greater detail with reference to Examples. However, the present invention is not limited to the following Examples, as long as the gist of the present invention does not depart from the following descriptions.

In the following, "part" means "part by mass."

A polyvinyl (PVA) alcohol polymer was prepared, and tablets were produced from an unmodified polyvinyl alcohol obtained by saponifying the obtained PVA polymer, as follows. The PVA polymer was measured for degree of saponification, and 4 mass % aqueous solution viscosity. The tablets were measured for hardness, and evaluated for friability and sustained release. The measurements were performed according to the following methods.

Degree of Saponification

Degree of saponification was measured according to the JIS K6726 method.

4 Mass % Aqueous Solution Viscosity

4 Mass % aqueous solution viscosity was measured according to the JIS K6726 method.

Hardness Evaluation

Hardness was evaluated with a Monsanto hardness tester.

Friability Evaluation

The tablet was placed in a tablet friability apparatus (available from Electrolab, India), and the drum was rotated at 25 rpm for 4 min. The mass of the tablet was then measured outside of the drum. The tablet friability was calculated as follows. In the equation, "mass loss" is obtained by subtracting the tablet mass after the testing from the initial tablet mass.

Percent Friability=(mass loss/initial tablet mass)×100

Sustained Release

Suitability as a pharmaceutical tablet was evaluated after stirring the tablet in 900 mL of phosphate buffer (pH 6.8) at 50 rpm at 37±0.5° C., using a Dissolution Apparatus Type I (TDT-08L available from Electrolab, India). The solution (5 ml) was sampled at certain time intervals, and the amount of metformin hydrochloride that had dissolved out of the tablet was measured at 233 nm, using a UV spectrophotometer (V-530 available from Jasco).

Tablet Shape

The shape of the molded tablet was visually inspected, and evaluated according to the following criteria.

Smooth: The tablet surface was smooth and did not discharge powders

Rough: The tablet surface had a rough texture and discharge powders

Example 1

Production of Polyvinyl Alcohol 1,000 Parts of vinyl acetate, 140 parts of methanol, and 0.05 mol % of azobisisobutyronitrile (relative to the vinyl acetate) were charged into a reaction vessel equipped with a reflux condenser, a dripping funnel, and an agitator. Heat was applied while stirring the mixture under a stream of nitrogen to allow polymerization for 5 hours below the boiling point. m-Dinitrobenzene was added to quench the polymerization upon completion of polymerization of 65% of the vinyl acetate, and the unreacted vinyl acetate monomers were removed out of the system under injected methanol steam to obtain a methanol solution of PVA polymer (resin content of 41%).

The methanol solution was furthermore diluted with methanol, and charged into a kneader after adjusting the concentration to 33%. At the maintained solution temperature of 40° C., a 3.5% methanol solution of sodium hydroxide was added in a proportion of 2.0 millimoles per mole of the vinyl acetate structure unit in the polymer to initiate saponification. A saponified product that precipitated out of the solution and formed particles in the course of saponification was filtered by solid-liquid separation.

The PVA dry powder had a degree of saponification of 87.7 mol % as measured by an analysis of the amount of alkali consumed for the hydrolysis of the residual vinyl acetate. The viscosity of a 4 mass % aqueous solution was 41.5 mPa·s, and the average degree of polymerization was 2,400.

The obtained PVA dry powder was introduced into methanol in a bath ratio of 10, and separated by solid-liquid separation after being stirred for 3 hours. The resulting PVA powder (50% particle size of 500 μm, sodium acetate content of 0.05 parts) was vacuum dried at 90° C. until the volatile content was 1% or less.

The sodium acetate content was determined through neutralization titration of a solution of the PVA powder in water with hydrochloric acid, using methyl orange as an indicator.

The obtained PVA dry powder was then pulverized to the target size via collision using a BI mill (available from MicroPowtec), and PVA fine particles (pulverized product) were obtained.

The particle size of the obtained PVA fine particles was measured with a laser diffraction particle size distribution measurement device (LMS-3000 available from Malvern) under a dispersive pressure of 2 to 4 bar over a time period of 1 second. The 50% particle size (D50) was 96 μm.

NMR Measurement

The obtained PVA dry powder was charged into a zireonia rotor having a diameter of 4 mm after adding the same amount of n-decane. Measurements were made at room temperature at a rotor rotation speed of 5,000 Hz under the conditions shown in Table 2. The obtained spectrum was separated into waveforms using a Gaussian function at 46 ppm, 41 ppm, 36 ppm, and 21 ppm, and the area of each waveform was calculated. The gauche structure, and the degree of saponification were calculated according to the following formulae (2) and (3).

Figure 2:
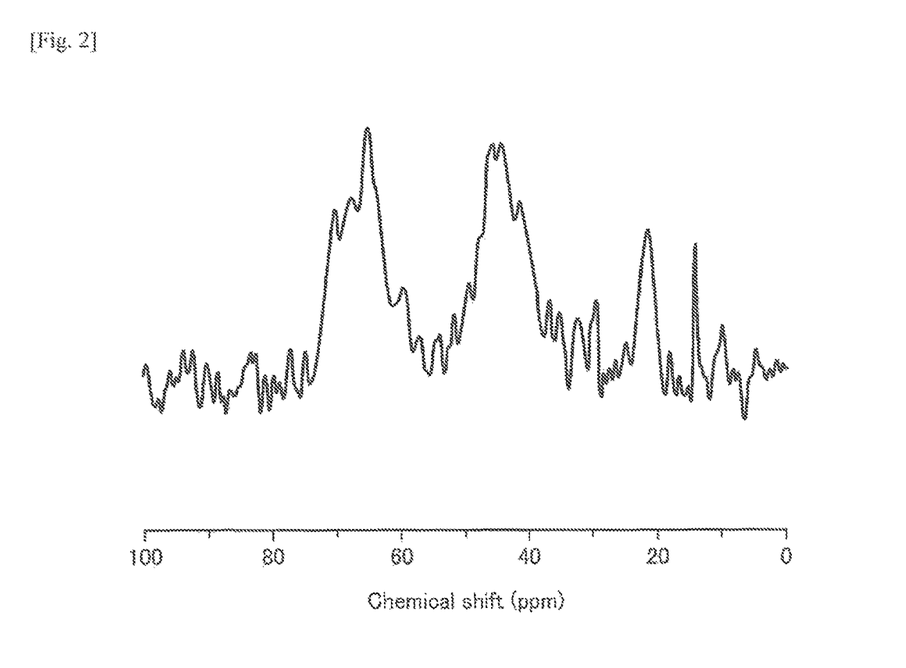
FIG. 2 shows a solid-state NMR chart of Examples 1 and 2.

The waveforms of the peaks are shown in FIG. 2.

$$\text{Gauche structure (mol \%)} = 100 \times (B/2 + C)/(A + B + C) \quad (2)$$

(In formula (2), A represents the peak area at 46 ppm, B represents the peak area at 41 ppm, and C represents the peak area at 36 ppm.)

$$\text{Degree of saponification (mol \%)} = 100 \times (1 - D/(A + B + C)) \quad (3)$$

(In formula (3), A represents the peak area at 46 ppm, B represents the peak area at 41 ppm, C represents the peak area at 36 ppm, and D represents the peak area at 21 ppm.)

TABLE 2

| Measurement conditions | |
|---|---|
| Device Probe | Bruker AVANCEIII 400WB CP/MAS probe (φ = 4 mm) |
| Temperature | Room temperature (22° C.) |
| Medium | n-clecane |
| Observed nucleus | $^{13}C$ |
| Rotation of sample tube | 5,000 Hz |
| $^{1}H$ 90° pulse | 4.2 μs |
| Contact time | 350 μs |
| τt | 72 μs |
| τd | 1 ms, 20 ms, 50 ms, 100 ms |
| FID signal capture time | 14 ms |
| Runs | >3,000 |
| Observation center | 120 ppm |
| Observation range | 365 ppm |
| Waiting time | 20 s |

Tablet Production

100 Parts of the obtained PVA fine particles, 100 parts of metformin hydrochloride, and 70 parts of crystalline cellulose (PH102 available from Asahi Kasei Chemicals Corporation) were mixed. The mixture was dissolved in IPA (isopropyl alcohol) and water (mass ratio of 50/50) with 30 parts of polyvinylpyrrolidone (PVP K 30 available from BASF) which is a solvent, using a granulator (Rapid Mixer Granulator available from Gem Pharma Machineries). After adding an appropriate amount, the mixture was granulated. The granules were dried with a Tray dryer (available from Bombay Machines) until the residual moisture was 2 to 4 w/w %, and a granulated material was obtained.

The granulated material was mixed with 30 parts of crystalline cellulose PH102, 3 parts of Aerosil, and 1 part of magnesium stearate, and an ellipsoidal tablet (measuring 1.9 cm in length, 0.9 cm in width, and 0.5 cm in height) was produced using a rotary tablet press.

Figure 4:
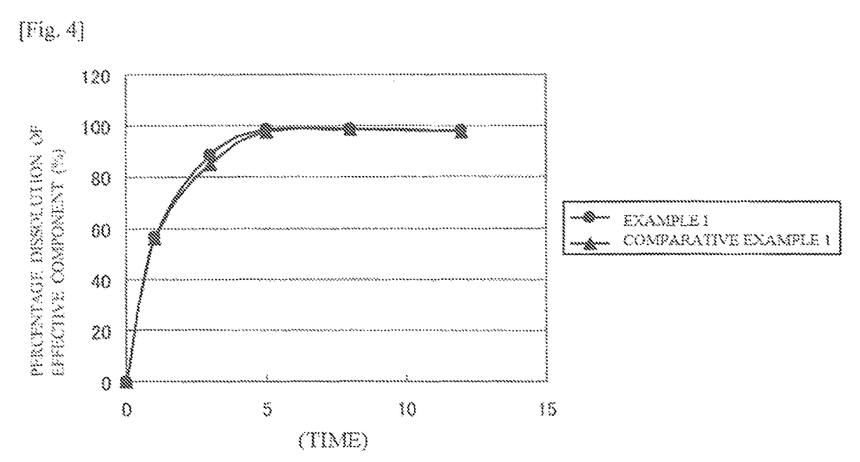
FIG. 4 is a diagram representing the percentage dissolution of active ingredient of Example 1 and Comparative Example 1.

The tablet was measured for hardness, friability, molded shape, and dissolution time. The results are shown in Table 3. The tablet was also evaluated for sustained release. The result is shown in FIG. 4.

Comparative Example 1

A polyvinyl alcohol powder (degree of saponification: 87.7 mol %, the viscosity of a 4 mass % aqueous solution: 41.5 mPa·s) was pulverized, introduced into methanol in a bath ratio of 10, and stirred for 3 hours. After solid-liquid separation, the resulting PVA fine particles were vacuum dried at 90° C. until the volatile content was 1% or less. This produced PVA fine particles.

The 50% particle size (D50) was 100 μm as measured with a laser diffraction particle size distribution measurement device.

Figure 3:
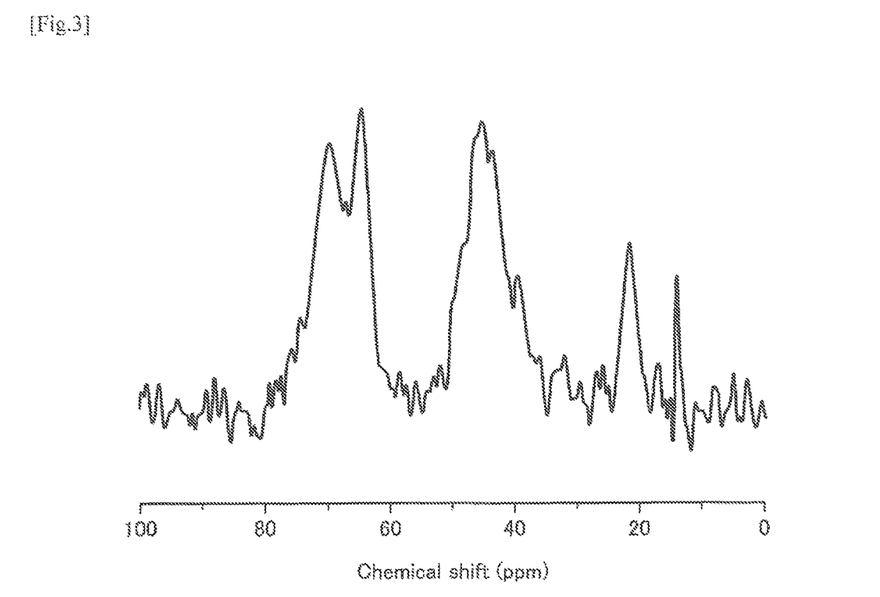
FIG. 3 shows a solid-state NMR chart of Comparative Examples 1 and 2.

The gauche structure and the degree of saponification were determined by calculations through NMR measurements performed in the same manner as in Example 1. The waveforms are shown in FIG. 3.

The PVA was used to produce a tablet, and the tablet was evaluated, as in Example 1. The results are shown in Table 3. The result of a sustained release test is shown in FIG. 4.

Example 2

500 Parts of metformin hydrochloride was dissolved in IPA and water (mass ratio of 50/50) with 100 parts of polyvinylpyrrolidone (PVP K 30 available from BASF) which is a solvent, using a granulator (Rapid Mixer Granulator available from Gem Pharma Machineries). After adding an appropriate amount, the mixture was granulated.

The granulated material was mixed with 500 parts of the PVA fine particles obtained in Example 1, and 10 parts of magnesium stearate. An ellipsoidal tablet (measuring 1.9 cm in length, 0.9 cm in width, and 0.5 cm in height) was then produced using a rotary tablet press.

Figure 5:
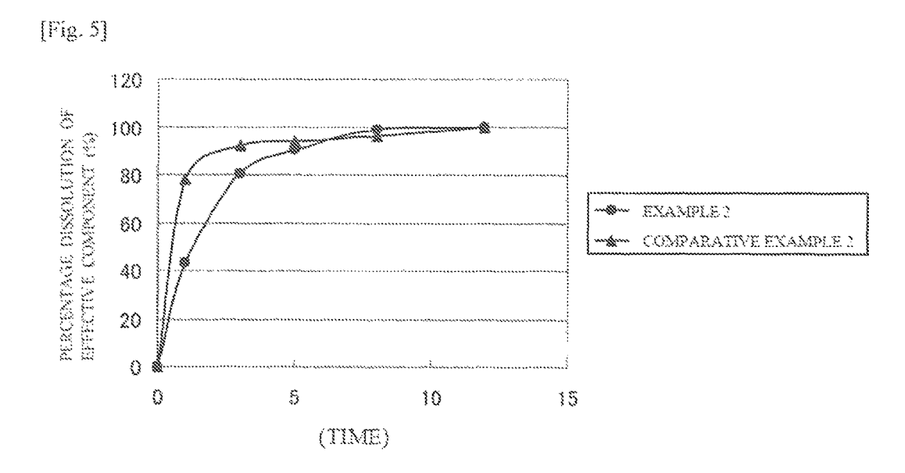
FIG. 5 is a diagram representing the percentage dissolution of active ingredient of Example 2 and Comparative Example 2.

The tablet was evaluated in the same manner as in Example 1. The results are shown in Table 3. The result of a sustained release test is shown in FIG. 5.

Comparative Example 2

The PVA fine particles produced in Comparative Example 1 were used to produce a tablet in the same manner as in Example 2, and the tablet was evaluated. The results are shown in Table 3. The result of a sustained release test is shown in FIG. 5.

TABLE 3

| | Particle size (μm) | Hardness (kg) | Friability (%) | Shape of molded tablet | Gauche structure (mol %) | Degree of surface saponification (mol %) | Ratio of saponification degrees (average/surface) |
|---|---|---|---|---|---|---|---|
| Ex. 1 | 96 | 5 | 0.1 | Smooth | 36 | 78 | 1.14 |
| Com. Ex. 1 | 100 | 3 | 0.2 | Rough | 23 | 82 | 1.08 |
| Ex. 2 | 96 | 5 | 1.6 | Smooth | 36 | 78 | 1.14 |
| Com. Ex. 2 | 100 | 1 | 4 | Rough | 23 | 82 | 1.08 |

By comparing Example 1 and Comparative Example 1 in which the PVA fine particles were added at the time of granulation, the tablet of Example 1 had more desirable hardness and friability than the tablet of Comparative Example 1, despite that the particle sizes were about the same.

The obtained tablet also had a smoother surface. The performance level of sustained release was about the same in Example 1 and Comparative Example 1.

By comparing Example 2 and Comparative Example 2 in which the PVA fine powder was added at the time of compression molding after granulation, the tablet of Example 2 had more desirable hardness and friability than the tablet of Comparative Example 2, despite that the particle sizes were about the same. The tablet of Example 2 also had a smoother surface. The performance level of sustained release was more desirable in Example 2 than in Comparative Example 2.

As demonstrated above, by using the medical binder as the PVA fine particles of the present invention, a tablet of desirable properties including moldability, hardness, sustained release, and friability can be obtained.

While the present invention has been described in detail and with reference to a certain embodiment of the invention, it will be apparent to a skilled person that various changes and modifications may be made thereto without departing from the spirit and scope of the invention. The present application is based on Japanese Patent Application No. 2014-152290 filed on Jul. 25, 2014, the entire contents of which are hereby incorporated by reference.

The invention claimed is:

1. A polyvinyl alcohol fine particle, comprising: 25 mol % or more of a gauche structure in polyvinyl alcohol molecules within a 0.8-nm region inside the particle from the particle surface wherein the ratio (S1/S2) of an average degree of saponification (S1) of the polyvinyl alcohol fine particle to an average degree of surface saponification (S2) in the 0.8-nm region inside the particle from the particle surface is 1.10 or more.

2. The polyvinyl alcohol fine particle according to claim 1, which is obtained by pulverizing a dry powder of a polyvinyl alcohol consisting of solely a vinyl alcohol structure unit and a vinyl ester structure unit.

3. The polyvinyl alcohol fine particle according to claim 2, wherein a 50% particle size of the dry powder of the polyvinyl alcohol is 50 to 2,000 μm.

4. The polyvinyl alcohol fine particle according to claim 1, wherein a 50% particle size of the polyvinyl alcohol fine particle is 1 to 200 μm.

5. The polyvinyl alcohol fine particle according to claim 1, which has an average degree of polymerization of 200 to 4,000.

6. The polyvinyl alcohol fine particle according to claim 1, comprising: an alkali metal salt in an amount of 0.001 to 2 mass % of the polyvinyl alcohol fine particle.

7. A pharmaceutical binder, comprising: the polyvinyl alcohol fine particle of claim 1.

8. A pharmaceutical tablet, comprising: an active ingredient; and the pharmaceutical binder of claim 7.

9. A sustained-release pharmaceutical tablet, comprising: an active ingredient; and the pharmaceutical binder of claim 7.

10. A method for producing the polyvinyl alcohol fine particle according to claim 1, comprising: washing and drying a polyvinyl alcohol obtained from a vinyl alcohol structure unit and a vinyl ester structure unit, and pulverizing an obtained dry powder of the polyvinyl alcohol.

* * * * *